(12) United States Patent
Servidio

(10) Patent No.: US 10,231,840 B2
(45) Date of Patent: Mar. 19, 2019

(54) LOW PROFILE TIBIAL BASEPLATE WITH FIXATION MEMBERS

(71) Applicant: Howmedica Osteonics Corp., Mahwah, NJ (US)

(72) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 133 days.

(21) Appl. No.: 15/220,603

(22) Filed: Jul. 27, 2016

(65) Prior Publication Data

US 2018/0028323 A1    Feb. 1, 2018

(51) Int. Cl.
*A61F 2/38*      (2006.01)
*A61F 2/30*      (2006.01)

(52) U.S. Cl.
CPC .... *A61F 2/389* (2013.01); *A61F 2002/30841* (2013.01); *A61F 2002/30878* (2013.01); *A61F 2002/30881* (2013.01); *A61F 2002/30889* (2013.01); *A61F 2002/30894* (2013.01); *A61F 2002/30897* (2013.01); *A61F 2002/30899* (2013.01); *A61F 2220/0016* (2013.01)

(58) Field of Classification Search
CPC .............. A61F 2/389; A61F 2220/0016; A61F 2002/30878; A61F 2002/30889; A61F 2002/30899; A61F 2002/30894
See application file for complete search history.

(56) References Cited

U.S. PATENT DOCUMENTS

| 3,798,679 A | 3/1974 | Ewald |
| 3,816,855 A | 6/1974 | Saleh |
| 3,869,731 A | 3/1975 | Waugh et al. |

(Continued)

FOREIGN PATENT DOCUMENTS

| EP | 0306744 A2 | 3/1989 |
| EP | 1011542 A1 | 6/2000 |

(Continued)

OTHER PUBLICATIONS

Howmedica, Inc. The Howmedica Kinematic Knee System, 1980.

(Continued)

*Primary Examiner* — David H Willse
*Assistant Examiner* — Javier Blanco
(74) *Attorney, Agent, or Firm* — Lerner, David, Littenberg, Krumholz & Mentlik, LLP

(57) ABSTRACT

A tibial baseplate may include a bridge portion connecting medial and lateral condylar portions at an anterior end portion of the baseplate, and a pair of fixation members extending inferiorly from a bone contacting surface of each of the medial and lateral condylar portions. One of each pair of fixation members may extend posteriorly from the bone contacting surface, may be positioned anterior to the other of the pair, and may include at least one recessed surface. The recessed surface may include a lateral recess, a posterior recess, and a medial recess. During insertion of the tibial baseplate into the bone, one of each pair of fixation members may guide the tibial baseplate into the bone and secure the tibial baseplate, while the other of each pair of fixation members may drag along the bone so that bone chips accumulate in the recesses, providing for increased fixation of the baseplate.

17 Claims, 8 Drawing Sheets

(56) References Cited

U.S. PATENT DOCUMENTS

| | | | |
|---|---|---|---|
| 4,207,627 A | 6/1980 | Cloutier | |
| 4,586,933 A | 5/1986 | Shoji et al. | |
| 4,634,444 A | 1/1987 | Noiles | |
| 4,711,639 A | 12/1987 | Grundei | |
| 4,769,040 A | 9/1988 | Wevers | |
| 4,822,362 A | 4/1989 | Walker et al. | |
| 5,037,439 A | 8/1991 | Albrektsson et al. | |
| 5,137,536 A | 8/1992 | Koshino | |
| 5,171,283 A | 12/1992 | Pappas et al. | |
| 5,207,711 A * | 5/1993 | Caspari | A61F 2/38 623/20.3 |
| 5,282,868 A | 2/1994 | Bahler | |
| 5,509,934 A | 4/1996 | Cohen | |
| 5,593,448 A | 1/1997 | Dong | |
| 5,609,641 A | 3/1997 | Johnson et al. | |
| 5,658,341 A | 8/1997 | Delfosse | |
| 5,702,464 A | 12/1997 | Lackey et al. | |
| 5,702,467 A | 12/1997 | Gabriel et al. | |
| 5,755,801 A | 5/1998 | Walker et al. | |
| 5,824,103 A | 10/1998 | Williams | |
| 5,879,394 A | 3/1999 | Ashby et al. | |
| 5,951,603 A | 9/1999 | O'Neil et al. | |
| 6,010,534 A | 1/2000 | O'Neil et al. | |
| 6,258,127 B1 | 7/2001 | Schmotzer | |
| 6,387,131 B1 | 5/2002 | Miehlke et al. | |
| 6,436,145 B1 | 8/2002 | Miller | |
| 6,482,209 B1 | 11/2002 | Engh et al. | |
| 6,558,421 B1 | 5/2003 | Fell et al. | |
| 6,625,526 B2 | 9/2003 | Gras | |
| 6,652,588 B2 | 11/2003 | Hayes, Jr. et al. | |
| 6,679,914 B1 | 1/2004 | Gabbay | |
| 6,699,291 B1 | 3/2004 | Augoyard et al. | |
| 6,896,702 B2 | 5/2005 | Collazo | |
| 6,969,393 B2 | 11/2005 | Pinczewski et al. | |
| 7,060,101 B2 | 6/2006 | O'Connor et al. | |
| 7,066,963 B2 | 6/2006 | Naegerl | |
| 7,115,131 B2 | 10/2006 | Engh et al. | |
| 7,189,262 B2 | 3/2007 | Hayes, Jr. et al. | |
| 7,261,740 B2 | 8/2007 | Tuttle et al. | |
| 7,294,149 B2 | 11/2007 | Hozack et al. | |
| 7,458,933 B2 | 12/2008 | LeVahn et al. | |
| 7,462,199 B2 | 12/2008 | Justin et al. | |
| 7,578,850 B2 * | 8/2009 | Kuczynski | A61F 2/38 623/20.21 |
| 7,625,407 B2 | 12/2009 | Akizuki et al. | |
| 7,635,390 B1 | 12/2009 | Bonutti | |
| 7,695,519 B2 | 4/2010 | Collazo | |
| 7,708,782 B2 | 5/2010 | Burstein et al. | |
| 7,758,652 B2 | 7/2010 | Engh et al. | |
| 7,766,969 B2 | 8/2010 | Justin et al. | |
| 7,771,483 B2 | 8/2010 | Justin et al. | |
| 7,771,484 B2 | 8/2010 | Campbell | |
| 7,799,086 B2 | 9/2010 | Justin et al. | |
| 7,828,852 B2 | 11/2010 | Bonutti | |
| 7,828,853 B2 | 11/2010 | Ek et al. | |
| 7,947,082 B2 | 5/2011 | Guidera et al. | |
| 7,988,736 B2 | 8/2011 | May et al. | |
| 8,002,777 B2 | 8/2011 | Fox et al. | |
| 8,066,776 B2 | 11/2011 | O'Connor et al. | |
| 8,092,546 B2 | 1/2012 | Coon et al. | |
| 8,105,387 B2 | 1/2012 | Barnett et al. | |
| 8,114,165 B2 | 2/2012 | Rhodes et al. | |
| 8,128,703 B2 | 3/2012 | Hazebrouck et al. | |
| 8,137,407 B2 | 3/2012 | Todd et al. | |
| 8,157,869 B2 | 4/2012 | Metzger et al. | |
| 8,211,181 B2 | 7/2012 | Walker | |
| 8,292,964 B2 | 10/2012 | Walker | |
| 8,292,965 B2 | 10/2012 | Walker | |
| 8,343,227 B2 | 1/2013 | Metzger et al. | |
| 8,403,994 B2 | 3/2013 | Maloney et al. | |
| 8,500,818 B2 | 8/2013 | Metzger et al. | |
| 8,529,631 B2 | 9/2013 | Donno et al. | |
| 8,568,486 B2 | 10/2013 | Wentorf et al. | |
| 8,574,304 B2 | 11/2013 | Wentorf et al. | |
| 8,603,101 B2 | 12/2013 | Claypool et al. | |
| 8,613,775 B2 | 12/2013 | Wentorf et al. | |
| 8,682,052 B2 | 3/2014 | Fitz et al. | |
| 8,690,955 B2 | 4/2014 | Rolston | |
| 8,728,167 B2 | 5/2014 | Collazo | |
| 8,771,365 B2 | 7/2014 | Bojarski et al. | |
| 8,894,715 B2 | 11/2014 | Metzger et al. | |
| 8,906,107 B2 | 12/2014 | Bojarski et al. | |
| 8,911,501 B2 | 12/2014 | Irwin et al. | |
| 9,271,840 B2 | 3/2016 | Keggi et al. | |
| 9,345,578 B2 | 5/2016 | Collazo et al. | |
| 2004/0025926 A1 | 2/2004 | Gin et al. | |
| 2004/0030397 A1 | 2/2004 | Collazo | |
| 2004/0138755 A1 | 7/2004 | O'Connor et al. | |
| 2005/0125068 A1 * | 6/2005 | Hozack | A61F 2/389 623/20.32 |
| 2005/0283251 A1 | 12/2005 | Coon et al. | |
| 2006/0004460 A1 | 1/2006 | Engh et al. | |
| 2006/0195196 A1 | 8/2006 | Pendleton et al. | |
| 2006/0212124 A1 | 9/2006 | Siebel | |
| 2006/0265079 A1 | 11/2006 | D'Alessio | |
| 2007/0010890 A1 | 1/2007 | Collazo | |
| 2007/0173858 A1 | 7/2007 | Engh et al. | |
| 2007/0203582 A1 | 8/2007 | Campbell | |
| 2008/0119941 A1 | 5/2008 | Seo et al. | |
| 2008/0183177 A1 * | 7/2008 | Fox | A61B 17/1604 606/88 |
| 2008/0200957 A1 * | 8/2008 | Marcacci | A61F 2/30721 606/329 |
| 2009/0187251 A1 | 7/2009 | Justin et al. | |
| 2009/0270995 A1 | 10/2009 | Rhodes et al. | |
| 2009/0319048 A1 | 12/2009 | Shah et al. | |
| 2010/0016980 A1 | 1/2010 | Donno et al. | |
| 2010/0131071 A1 | 5/2010 | O'Connor et al. | |
| 2010/0280624 A1 | 11/2010 | Engh et al. | |
| 2010/0305575 A1 | 12/2010 | Wilkinson et al. | |
| 2010/0305710 A1 | 12/2010 | Metzger et al. | |
| 2010/0305711 A1 | 12/2010 | McKinnon et al. | |
| 2010/0331847 A1 | 12/2010 | Wilkinson et al. | |
| 2010/0331848 A1 | 12/2010 | Smith et al. | |
| 2010/0331991 A1 | 12/2010 | Wilkinson et al. | |
| 2011/0015749 A1 | 1/2011 | Engh et al. | |
| 2011/0066248 A1 | 3/2011 | Ries et al. | |
| 2011/0066249 A1 | 3/2011 | Justin et al. | |
| 2011/0082559 A1 | 4/2011 | Hartdegen et al. | |
| 2011/0098824 A1 | 4/2011 | Jukes et al. | |
| 2011/0190898 A1 | 8/2011 | Lenz et al. | |
| 2011/0264097 A1 | 10/2011 | Hodorek et al. | |
| 2012/0035736 A1 | 2/2012 | O'Connor et al. | |
| 2012/0078262 A1 | 3/2012 | Pinczewski et al. | |
| 2012/0179266 A1 | 7/2012 | Collazo | |
| 2012/0209394 A1 | 8/2012 | Bojarski et al. | |
| 2012/0316563 A1 | 12/2012 | Metzger et al. | |
| 2012/0330429 A1 | 12/2012 | Axelson, Jr. et al. | |
| 2013/0006375 A1 | 1/2013 | Metzger et al. | |
| 2013/0024001 A1 | 1/2013 | Wentorf et al. | |
| 2013/0046385 A1 | 2/2013 | Hartdegen et al. | |
| 2013/0131817 A1 | 5/2013 | Parisi et al. | |
| 2013/0131819 A1 | 5/2013 | Parisi et al. | |
| 2013/0173010 A1 | 7/2013 | Irwin et al. | |
| 2013/0204383 A1 | 8/2013 | Wentorf | |
| 2013/0218284 A1 | 8/2013 | Eickmann et al. | |
| 2013/0245777 A1 | 9/2013 | Jerry | |
| 2013/0289731 A1 | 10/2013 | Katerberg et al. | |
| 2013/0345820 A1 | 12/2013 | Maloney et al. | |
| 2014/0025175 A1 | 1/2014 | Wentorf et al. | |
| 2014/0025176 A1 | 1/2014 | Wentorf et al. | |
| 2014/0025177 A1 | 1/2014 | Wentorf et al. | |
| 2014/0067076 A1 | 3/2014 | Collazo | |

FOREIGN PATENT DOCUMENTS

| | | |
|---|---|---|
| FR | 2676916 A1 | 12/1992 |
| JP | S6411541 A | 1/1989 |
| WO | 9858603 A1 | 12/1998 |
| WO | 0076428 A1 | 12/2000 |
| WO | 2006012370 A2 | 2/2006 |
| WO | 2009158318 A1 | 12/2009 |
| WO | 2010006677 A1 | 1/2010 |
| WO | 2010138836 A2 | 12/2010 |

(56) References Cited

FOREIGN PATENT DOCUMENTS

| WO | 2010138841 A2 | 12/2010 |
|---|---|---|
| WO | 2010138850 A2 | 12/2010 |
| WO | 2010138854 A2 | 12/2010 |
| WO | 2010138857 A2 | 12/2010 |
| WO | 2011094540 A2 | 8/2011 |
| WO | 2012178031 | 12/2012 |
| WO | 2013101582 | 7/2013 |
| WO | 2013148954 | 10/2013 |

OTHER PUBLICATIONS

Howmedica, Inc. Cruciate-Condylar Total Knee Surgical Technique, 1979.
BioPro, Equalizer Modular Total Knee Replacement, date not known.
Townley Total Knee Prosthesis, Vitallium Alloy Femoral Component, 1978.
Freeman-Swanson Total Knee Prosthesis, Vitallium Alloy Femoarl Component, 1978.
International Search Report and Written Opinion, PCT/US2012/0020719, dated Mar. 19, 2012.
Pritchett, James W., BioPro: Equalizer Modular Total Knee Replacement, available at least as early as 1999, 19 pages.
Townley, Charles 0., Total Knee Arthroplasty: A Personal Retrospective and Prospective Review, Clinical Orthopaedics and Related Research, No. 236, 1988, 15 pages.
Partial International Search Report for Application No. PCT/US2014/017664 dated Apr. 16, 2014.
Townley, Charles O., Total Knee Arthroplasty: A Personal Retrospecteive and Prospective Review, Clinical Orthopaedics and Related Research, No. 236, 1988, 15 pages.
International Search Report and Written Opinion for International Application No. PCT/US2012/070531, dated May 27, 2013, 17 pages.
International Search Report and Written Opinion for Application No. PCT/US2014/017664 dated Jun. 6, 2014.

\* cited by examiner

LOW PROFILE TIBIAL BASEPLATE WITH FIXATION MEMBERS

BACKGROUND OF THE DISCLOSURE

This disclosure relates to an orthopedic implant having a bone contacting surface with fixation features to facilitate implantation of the implant into a bone surface. More particularly, it relates to a tibial implant which fixation features in the form of pegs that may be angled and/or have enhanced fixation designs.

Various orthopedic implants have used pegs to help stabilize the component after implantation. Various knee prostheses, either tibial components or femoral components, have pegs that are inserted into the condylar area to provide stability on implantation. Such pegs may help prevent rotation of the implant after implantation. For example, many tibial and femoral components are supplied with long central stems for engaging the medullary canal and pegs extending a short distance into the condylar areas of the knee to prevent rotational movement of the inserted prosthesis.

BRIEF SUMMARY

According to one aspect of the disclosure, a tibial baseplate includes a bridge portion connecting medial and lateral condylar portions at an anterior end portion of the baseplate, and two fixation members extending inferiorly from a bone contacting surface of each of the medial and lateral condylar portions. One of the two fixation members of each of the medial and lateral condylar portions may extend posteriorly from the bone contacting surface, may be positioned anterior to the other of the two fixation members, and may include at least one recessed surface. The at least one recessed surface of the one of the two fixation members of each of the medial and lateral condylar portions may include a lateral recess, a posterior recess, and a medial recess. The one of the two fixation members of each of the medial and lateral condylar portions may each include a non-recessed anterior surface. The one of the two fixation members of each of the medial and lateral condylar portions may each include a posterior-medial wall and a posterior-lateral wall that converge with the non-recessed anterior surface to form a pointed tip, the lateral recess, the posterior recess, and the medial recess. The one of the two fixation members of each of the medial and lateral condylar portions may each include a pointed tip. The pointed tips may each extend along a longitudinal axis orthogonal to the bone contacting surface. The other of the two fixation members of each of the medial and lateral condylar portions may each include a cylindrical shaft and a pointed tip.

According to another aspect of the disclosure, a tibial baseplate may include a superior surface, a bone contacting surface, a lateral condylar portion, a medial condylar portion spaced from the lateral condylar portion, and a bridge portion connecting the medial and lateral condylar portions at an anterior end portion of the baseplate. A first fixation member may extend inferiorly and posteriorly from the bone contacting surface of the lateral condylar portion. A second fixation member may extend inferiorly and posteriorly from the bone contacting surface of the medial condylar portion. A third fixation member may extend inferiorly from the bone contacting surface, and the third fixation member may be positioned medially and anteriorly of the first and second fixation members, and may include a plurality of radially projecting sections. The plurality of radially projecting sections may include a superiormost projecting section having a diameter greater than a diameter of an inferiormost projecting section. The third fixation member may include a plurality of recessed sections, each recessed section being positioned between an adjacent couple of the plurality of projecting sections. A diameter of each recessed section may be smaller than diameters of each of the adjacent couple of the plurality of projecting sections. An outer surface of each recessed section may have a concave profile. The first fixation member may extend along a first longitudinal axis, the second fixation member may extend along a second longitudinal axis, and the third fixation member may extend along a third longitudinal axis oblique to the first and second longitudinal axes. The third longitudinal axis may be orthogonal to the bone contacting surface.

According to a further aspect of the disclosure, a method of implanting a tibial baseplate into a proximal tibia may include creating a first recess in the proximal tibia, the first recess extending at an angle in a posterior and inferior direction, the first recess having a shape and orientation substantially corresponding to a shape and orientation of a first fixation member of the tibial baseplate. The method may also include inserting the first fixation member into the first recess prior to a second fixation member of the tibial baseplate contacting the proximal tibia. The method may further include continuing to insert the first fixation member into the first recess as the second fixation member drags along the proximal tibia. The first fixation may be further inserted into the first recess until at least one recess in the second fixation member at least partially fills with bone material. At least one recess may be created in the proximal tibia corresponding to the second fixation member prior to inserting the first fixation member into the first recess. The tibial baseplate may be inserted to a final implanted position so that an anterior surface of the second fixation member directly abuts native bone. The step of inserting the first fixation member into the first recess prior to the second fixation member of the tibial baseplate contacting the proximal tibia may include inserting the first fixation member along the angle. The step of continuing to insert the first fixation member into the first recess as the second fixation member drags along the proximal tibia may be performed with an impactor. The method may alternately be performed without creating any recesses in the proximal tibia corresponding to the second fixation member prior to the second fixation member contacting the proximal tibia.

DETAILED DESCRIPTION

In the following description, certain directional terms may be used. Generally, as used herein, "proximal" refers to a location closer to the heart, while "distal" refers to a location farther from the heart. "Superior" refers to a location closer to the head while "inferior" refers to a location closer to the feet. "Medial" refers to a location closer to the midline of the body, while "lateral" refers to a location farther away from the midline of the body. "Anterior" refers to a location closer to the front of the body, while "posterior" refers to a location closer to the back of the body. With reference to the figures provided, identical numbers generally refer to similar or identical features. When ranges of values are provided, it should be understood that all values within the provided range are included, as well as all ranges within the range provided. For example, a range of 2 to 8 includes the values of 3 and 4, as well as the ranges of 4 to 7, as well as 3 to 5.

Generally, the description below relates to primary and/or revision total knee arthroplasty ("TKA") procedures. More specifically, the description below relates to tibial implants and methods of implanting the tibial implants onto the tibia. It should be understood that this procedure generally is undertaken during a surgery in which the femur is also prepared to receive a prosthetic femoral component, which is not separately described in detail herein. The procedure(s) may also be undertaken simultaneously with other related procedures, such as patellar implantations, whether or not described herein.

Figure 1:
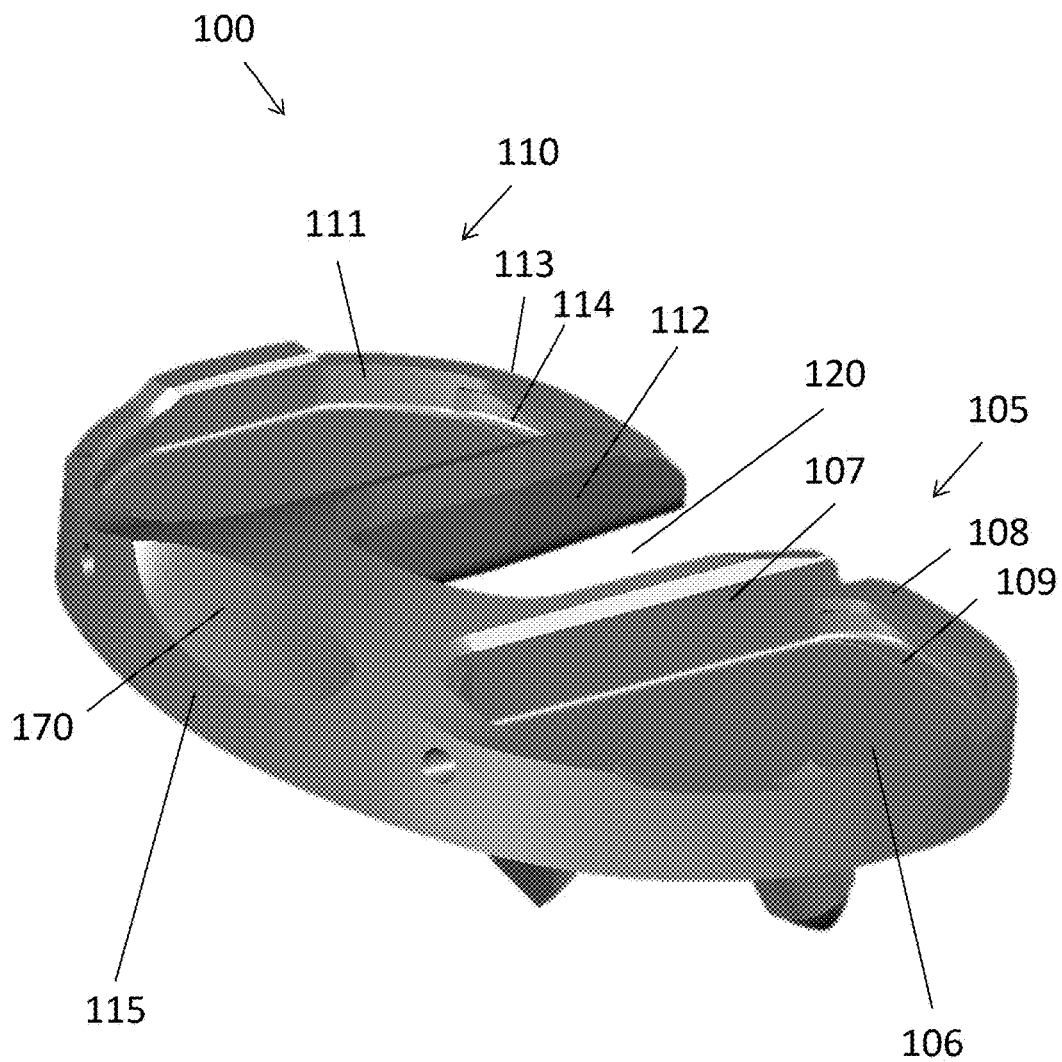
FIG. 1 is a top perspective view of a tibial baseplate according to an embodiment of the disclosure.
Figure 2:
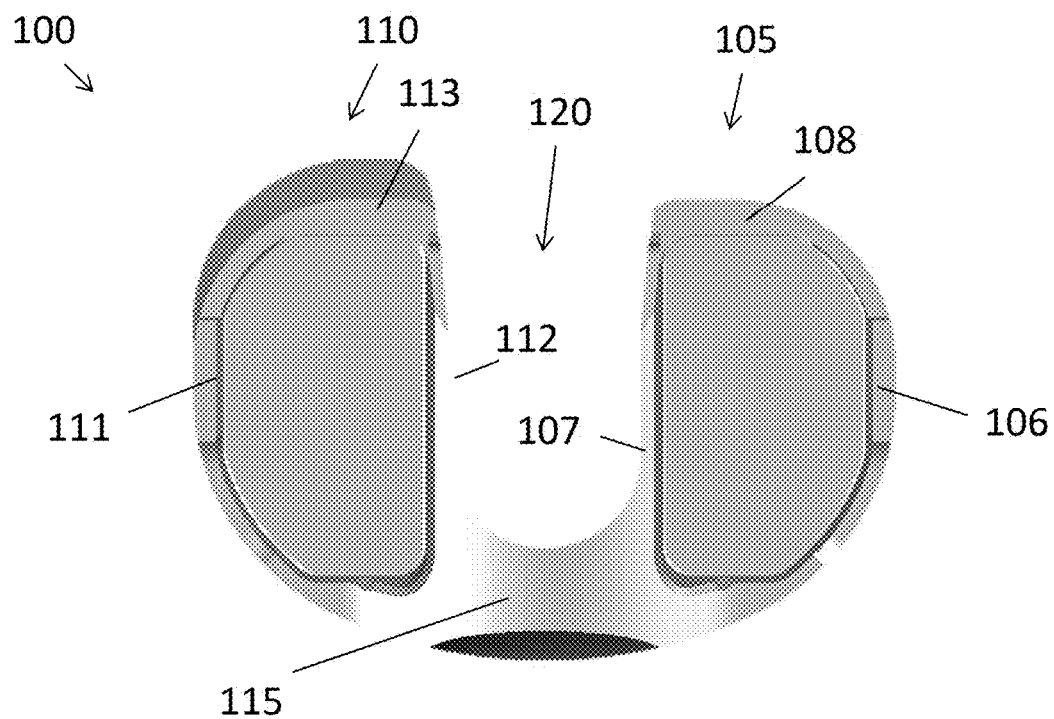
FIG. 2 is a top view of the tibial baseplate of FIG. 1.

Referring to FIGS. 1-2, there are shown top perspective and top views (looking at the superior surface when implanted), respectively, of a tibial baseplate or tray 100 according to an embodiment of the disclosure. Baseplate 100 includes a lateral condylar portion 105 and a medial condylar portion 110. In other words, the illustrated baseplate 100 would be for use to replace the proximal portion of a patient's left tibia. In other embodiments, lateral and medial condylar portions 105, 100 may be reversed such that baseplate 100 would be used to replace the proximal portion of a patient's right tibia. Portions 105, 110 are designed to receive a bearing insert (not shown), such as an ultra-high molecular weight polyethylene (UHMWPE) bearing component. The bearing inserts may provide a suitable surface against which the patient's knee (which may include a corresponding bearing surface of a femoral implant) may articulate. Such bearing inserts are described in greater detail, for example, in U.S. Pat. No. 9,345,578, the disclosure of which is hereby incorporated by reference herein. Lateral and medial condylar portions 105, 110 are connected by a bridge section 115. Lateral and medial condylar portions 105, 110 are preferably recessed and surrounded by a raised wall portion 106 laterally and 111 medially to locate the bearing inserts. Likewise, U-shaped eminence opening 120 is defined by lateral wall 107 and medial wall 112. Posterior walls 108 and 113 define the posterior end of the recesses in the lateral and medial condylar portions 105, 110, respectively. Undercut grooves 109, 114 may be located adjacent walls 108, 113 at the superiorly facing surface of condylar portions 105, 110 to allow the bearing inserts to be snapped into their respective condylar portions 105, 110. The bearing inserts may include corresponding grooves that snap or otherwise fit into a respective undercut groove 109, 114. The anterior and/or superior surface of bridge 115 may also include a recessed portion 170 which may help reduce sharp angles on the baseplate 100 that may otherwise irritate or interfere with tissue in the area, including tracking of the patella during knee joint motion. The anterior portions of condylar portions 105, 110 may also include apertures or through-holes on each side of recessed portion 170 to mate with components of inserts, such as locking components such as wires, to help secure the inserts within the respective condylar portions.

Figure 3:
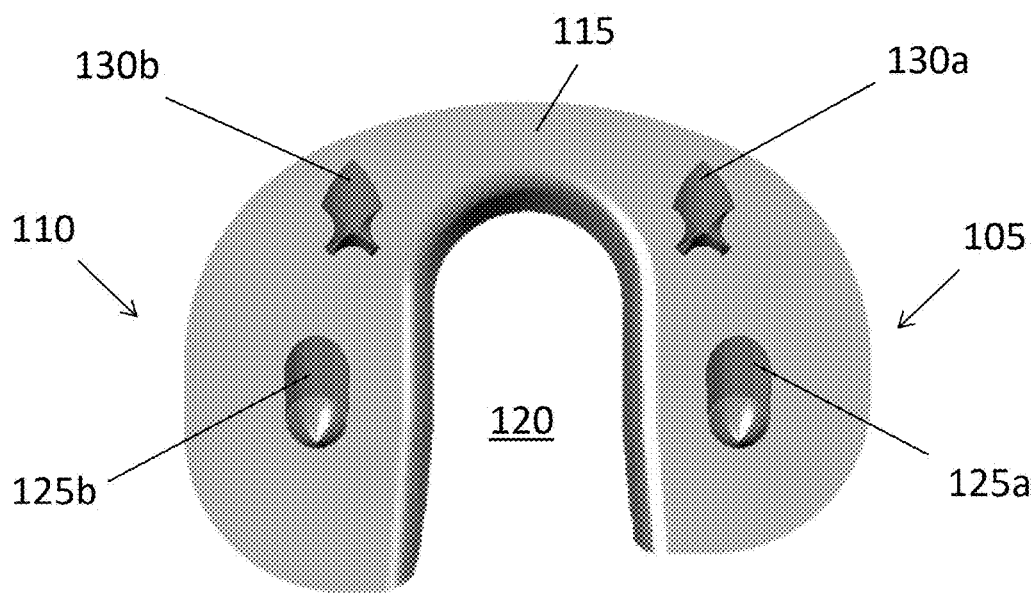
FIG. 3 is a bottom view of the tibial baseplate of FIG. 1.
Figure 4:
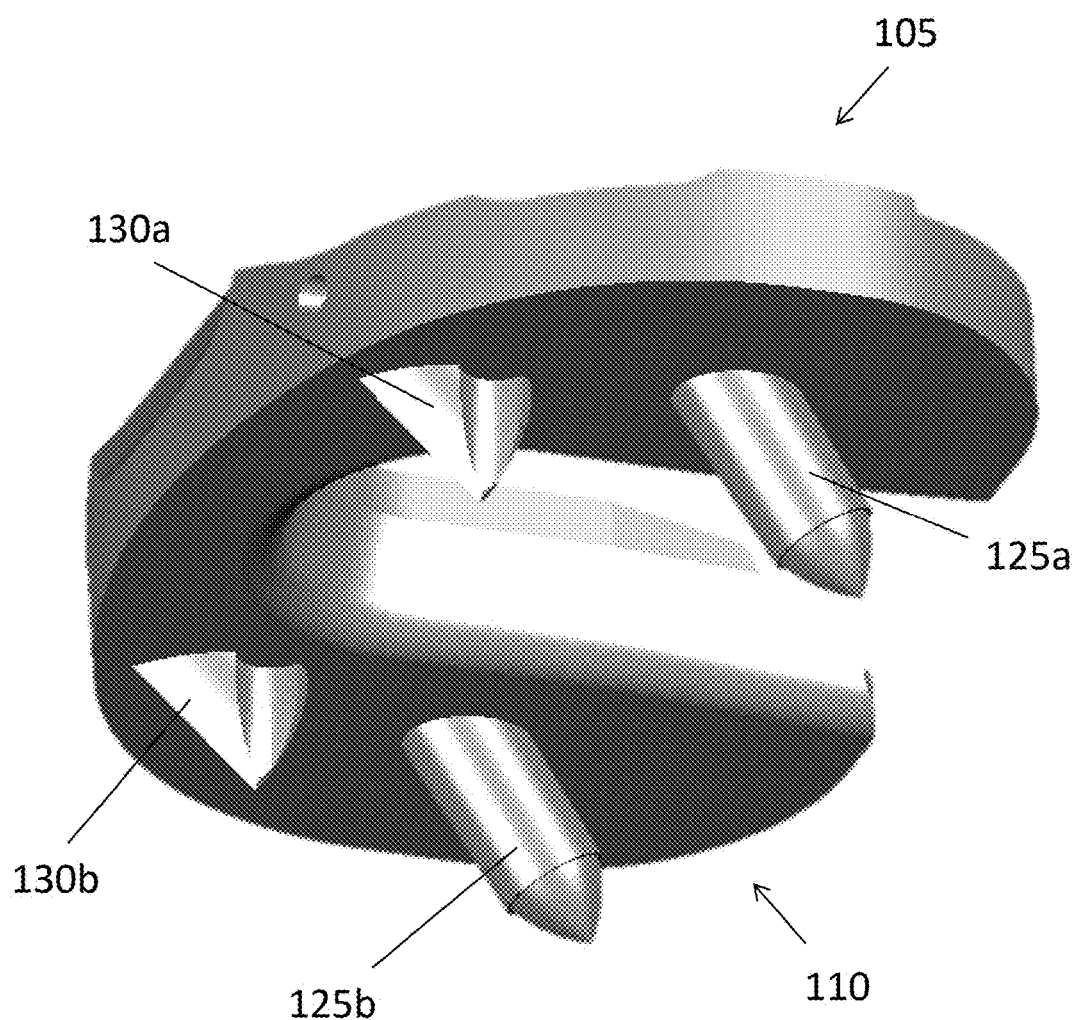
FIG. 4 is a bottom perspective of the tibial baseplate of FIG. 1.
Figure 5:
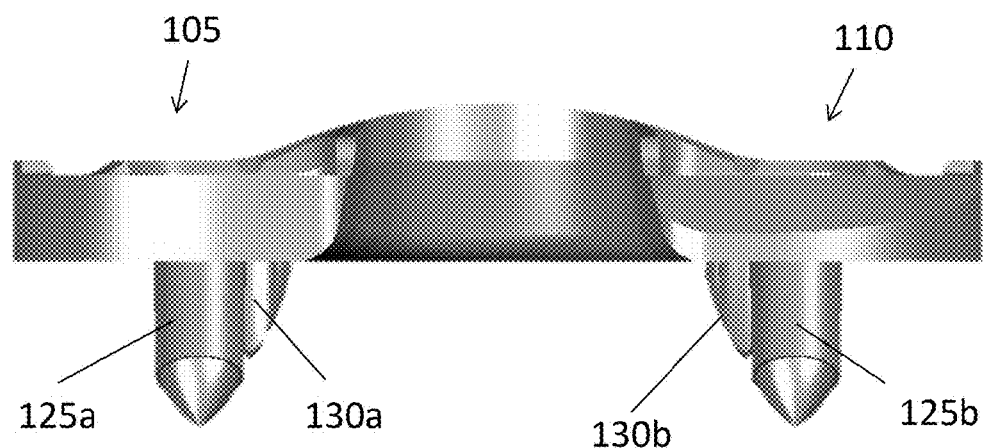
FIG. 5 is a rear view of the tibial baseplate of FIG. 1.
Figure 6:
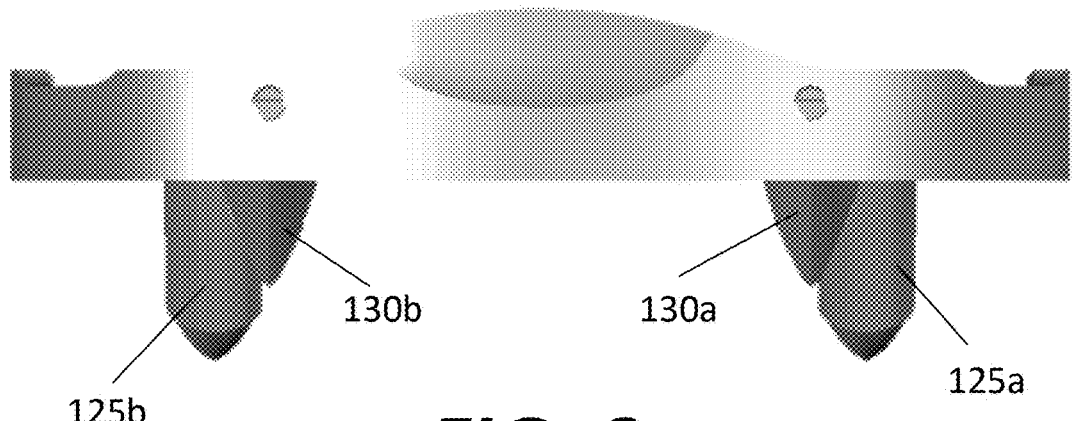
FIG. 6 is a front view of the tibial baseplate of FIG. 1.
Figure 7:
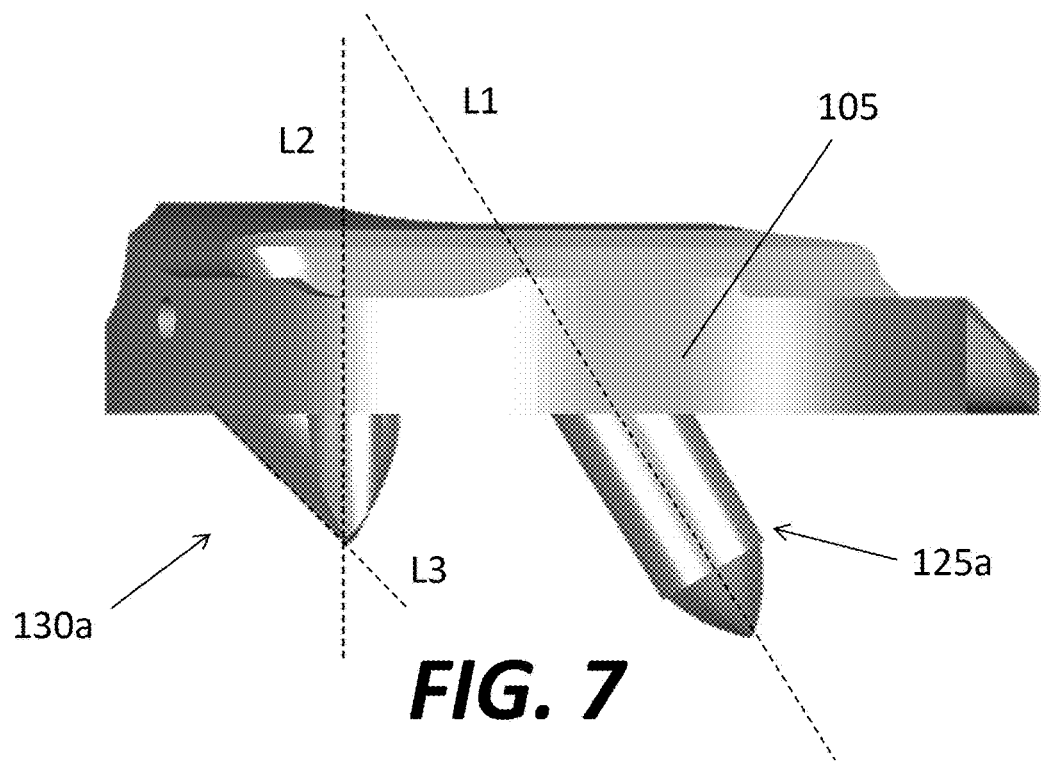
FIG. 7 is a side view of the tibial baseplate of FIG. 1.
Figure 8:
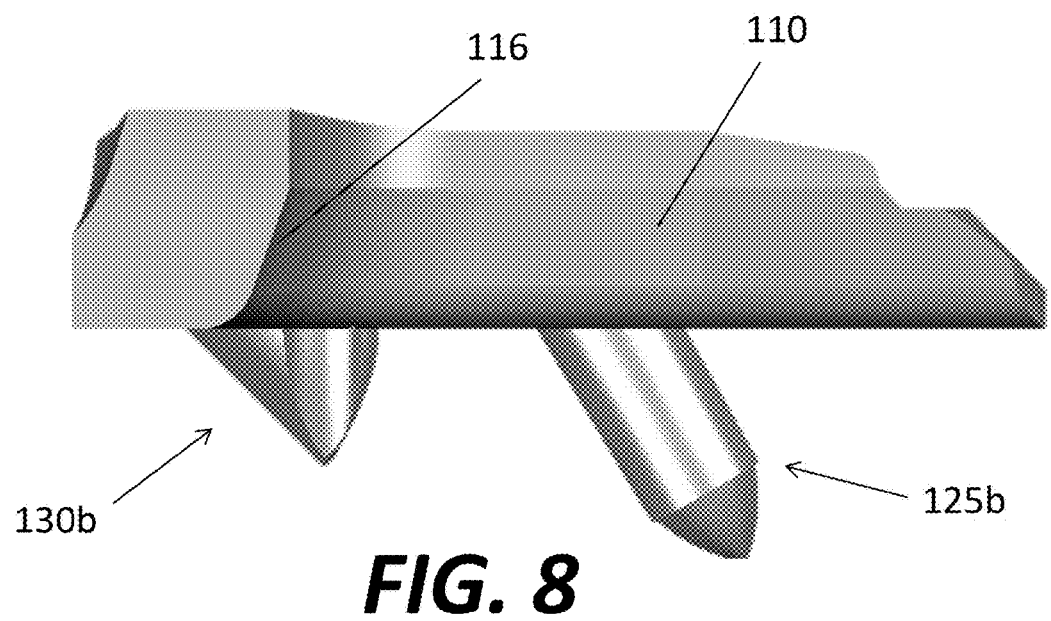
FIG. 8 is a cross-section of the tibial baseplate of FIG. 1.

Referring to FIGS. 3-4, there are shown bottom and bottom perspective views respectively, of baseplate 100 including the bone contacting surface. As seen, lateral portion 105 and medial portion 110 are separated by eminence opening 120 and are connected by anterior bridge 115 at the anterior end of the baseplate 100. The bottom surface of baseplate 100 may include a first pair of fixation members 125a,b and a second pair of fixation members 130a,b. FIGS. 5-6 show posterior and anterior views, respectively, of tibial baseplate 100. FIG. 7 shows a side view of baseplate 100, while FIG. 8 shows the side view of FIG. 7 taken along a section extending through the center of anterior bridge 115.

Fixation member 125a may generally take the form of a peg extending inferiorly and posteriorly at an angle, for example between approximately 20 degrees and approximately 60 degrees, from the bone-contact surface of the lateral condylar portion 105 of the baseplate 100 along a longitudinal axis L2 (see FIG. 7). Peg 125a may include a substantially cylindrical shaft portion that terminates in a pointed tip that has a substantially conical shape. Medial condylar portion 110 may include a fixation member 125b in the form of a peg that is identical or substantially identical to peg 125a, with the exception that peg 125b extends from the bone contacting surface of the lateral condylar portion 110 of baseplate 100. Fixation members 125a and 125b may be positioned at substantially equal locations in the anterior-posterior direction of baseplate 100 with respect to one another. This position may be at or substantially at the center of the condylar portions 105, 110 in the anterior-posterior direction. However, since the medial condylar portion 110 may be longer in the anterior-posterior direction than the lateral condylar portion 105 in some embodiments (as described in greater detail below), the pegs 125a, 125b may be slightly offset in the anterior-posterior direction so that each peg is positioned substantially at the center of the respective condylar portion 105, 110, or otherwise if the pegs 125a, 125b are exactly aligned in the anterior-posterior direction, one of the pegs 125a or 125b may be slightly off center from its condylar portion 105, 110 in the anterior-posterior direction. As should be understood, the pointed tips of the fixation members 125a, 125b may assist in securing the baseplate to a proximal tibia prepared to accept the baseplate 100. In some embodiments, the baseplate 100 may be forced, for example may impaction or another method, into the proximal tibia using force substantially aligned with the angle of the pegs 125a, 125b, with the pointed tips helping drive the pegs 125a, 125b into the bone. In other embodiments, a pilot hole or other recess may be formed in the proximal tibia to help guide the insertion of pegs 125a, 125b into the proximal tibia. Although pegs 125a, 125b are illustrated with pointed tips, other shapes may be acceptable including blunted tips.

Figure 9:
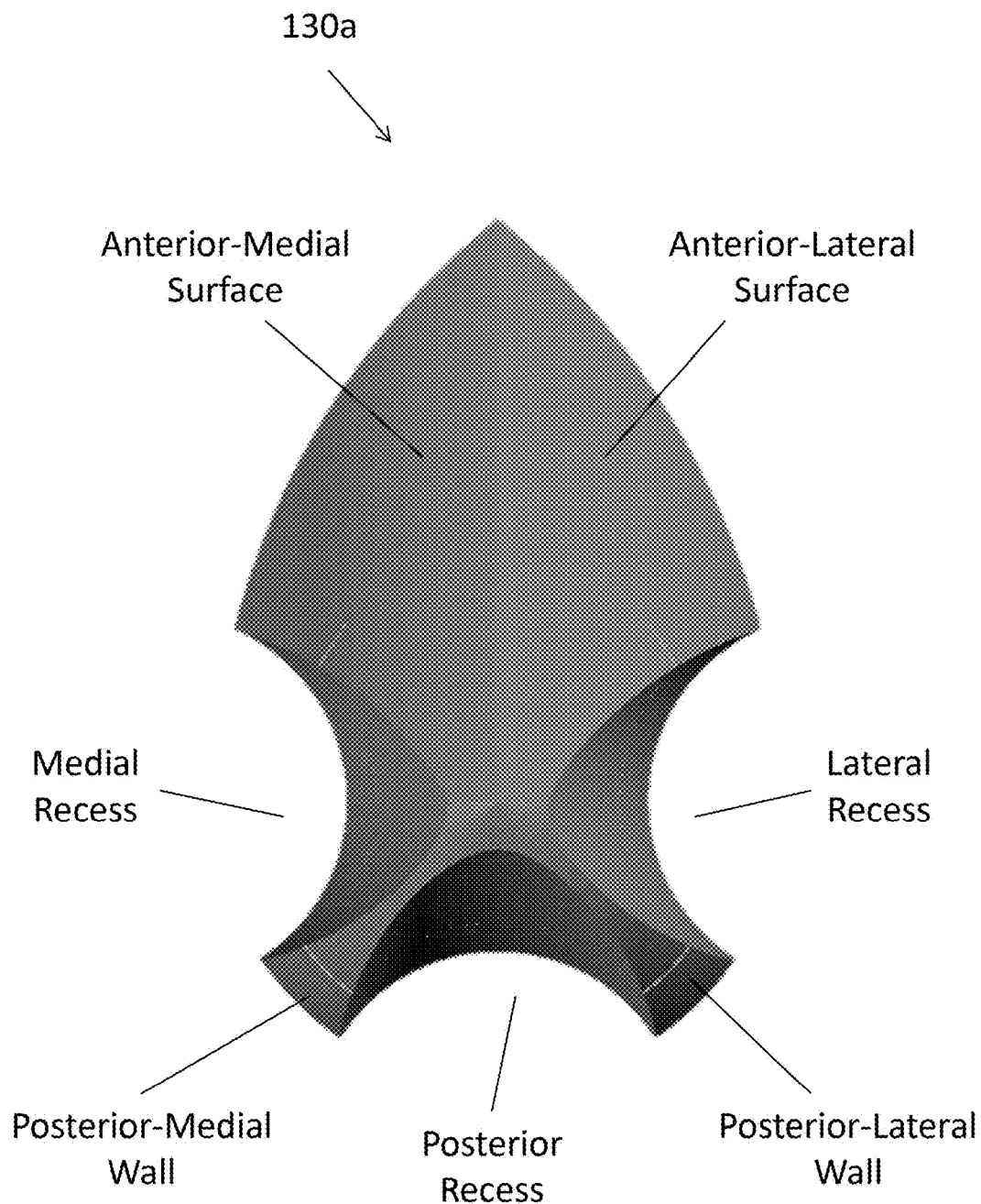
FIG. 9 is an isolated bottom view of a fixation member of the tibial baseplate of FIG. 1.

Fixation member 130a may be positioned on the bone contacting surface of lateral condylar portion 105 of baseplate 100 anterior to fixation member 125a. An enlarged isolated bottom view of fixation member 130a is shown in FIG. 9. Generally, fixation member 130a includes one or more recesses to collect bone or bone chips as fixation member 125a is driven into the proximal tibia. For example, in the embodiment shown, fixation member 130a includes a posterior-medial wall that joins a posterior-lateral wall to form a posterior recess. The posterior-lateral wall may join an anterior-lateral surface to form a lateral recess, and the posterior-medial wall may join an anterior-medial surface to form a medial recess. The anterior-medial surface may join the anterior-lateral surface without forming a recess. In the direction of insertion, the fixation member 130a will drag in the posterior direction across the proximal tibia, with bone chips being collected within the posterior, medial, and/or lateral recesses. Because of this, an anterior recess may not be necessary. The bone chips and recesses may assist in bone-ingrowth to better fix tibial baseplate 100 to the proximal tibia after initial implantation. The anterior surfaces and the posterior walls of fixation member 130a may meet at a sharp point to assist the fixation member 130a digging into the proximal tibia and being fixed therein. Fixation member 130b may have an identical or substantially identical structure to fixation member 130a. Similarly, fixation member 130b may be positioned on the bone contacting surface of medial condylar portion 110, anterior to peg 125b and closer to the midline of baseplate 100. As best seen in FIGS. 7-8, the anterior surfaces of fixation members 130a, 130b may extend in an inferior direction from the bone contacting surface of the baseplate and be angled posteriorly. The particular shape of fixation members 130a-b may be designed, at least in part, based on the angle of corresponding fixation members 125a-b. For example, the angle of fixation members 125a-b with respect to the bone-contacting surface of the baseplate 100 may be substantially equal to the angle of the anterior surface of corresponding fixation members 130a-b with respect to the bone-contacting surface of the baseplate 100.

It should be understood that, although fixation members 125a-b may each extend along a central longitudinal axis L1 that is angled with respect to the bone-contacting surface of the baseplate 100 (e.g. in an inferior-posterior direction), the fixation members 130a-b may each extend generally orthogonally to the bone-contacting surface of the baseplate 100. In other words, although the anterior-medial and anterior-lateral surfaces of the fixation members 130a-b may be angled, the tip of the point formed in the fixation members 130a-b may each be formed along a longitudinal axis L2 (see FIG. 7) that is substantially orthogonal to the bone-contacting surface of the baseplate 100. However, the anterior surfaces of the fixation members 130a-b may extend along an axis L3 with respect to the bone-contacting surface of the baseplate 100.

Referring now to FIG. 8, a posterior wall 116 of bridge 115 may be angled relative to the bone contacting surface of baseplate 100. Posterior wall 116 may be angled such that the inferior end portion of posterior wall 116 is positioned further anteriorly than the superior end portion of posterior wall 116. In this configuration, the posterior wall 116 of the bridge 115 generally exerts a downward force on an anterior portion of the tibial eminence, which may help provide a downward force to counteract the tendency of the ACL to lift the tibial eminence. Additionally, the angle of the posterior wall 116 of the bridge 115 minimizes the amount of tibial bone that must be removed anterior to the tibial eminence which helps maximize the bone strength.

In one embodiment, the dimension of the lateral condylar portion 105 in the anterior-posterior direction may be different than the dimension of the medial condylar portion 110 in the anterior-posterior direction, making each baseplate 100 asymmetric based on a desired alignment methodology or specific to the right/left knee, for example. Asymmetric tibial baseplates are shown, for example, in U.S. Pat. No. 8,911,501 titled "Cruciate Retaining Tibial Prosthesis," the disclosure of which is hereby incorporated by reference herein in its entirety. This extended dimension is illustrated particularly clearly in FIGS. 2 and 3. For example, the medial condylar portion 110 may be between approximately 0-6 millimeters larger in the anterior-posterior direction than the lateral condylar portion 105. Preferably, the medial condylar portion 110 is between approximately 3-5 millimeters larger in the anterior-posterior direction compared to the lateral condylar portion 105. The amount of extension of the medial condylar portion 110 in the anterior-posterior direction may be dependent on the size of the baseplate 100. It should be understood that, in other embodiments, the baseplate 100 need not have an opening to accommodate the tibial eminence, and may not need to have asymmetric lateral and medial condylar portions.

The angle of fixation members 125a-b may assist in implanting the baseplate 100 without needing as much clearance space as might otherwise be needed if the fixation members 125a-b were orthogonal to the bone-contacting surface of the baseplate 100. During implantation, pilot or other holes may or may not be pre-drilled into the proximal tibia to accept fixation members 125a-b. Similarly pilot or other holes may or may not be created in the proximal tibia to accept fixation members 130a-b, although it may be preferable to avoid such holes so that bone chips may gather within the recesses of fixation members 130a-b. An impactor or other tool may be used to drive the baseplate 100 into the proximal tibia. It should be understood that the tibial bone corresponding to the implant location of the baseplate 100 is likely to be relatively soft cancellous bone. As the fixation members 125a-b enter the bone, preferably along axis L1, the tip of fixation members 130a-b dig into the soft tibial bone, causing such bone to fill the recesses of the fixation members 130a-b. The anterior surfaces of fixation members 130a-b, after implantation is complete, are preferably flush with the remaining tibial bone anterior to the fixation members 130a-b. In order to accomplish this, it may be preferable that the anterior surfaces of fixation members 130a-b extend along a longitudinal axis L3 that is the same or more acute than axis L1 with respect to the bone-contacting surface of the baseplate 100.

Figure 10:
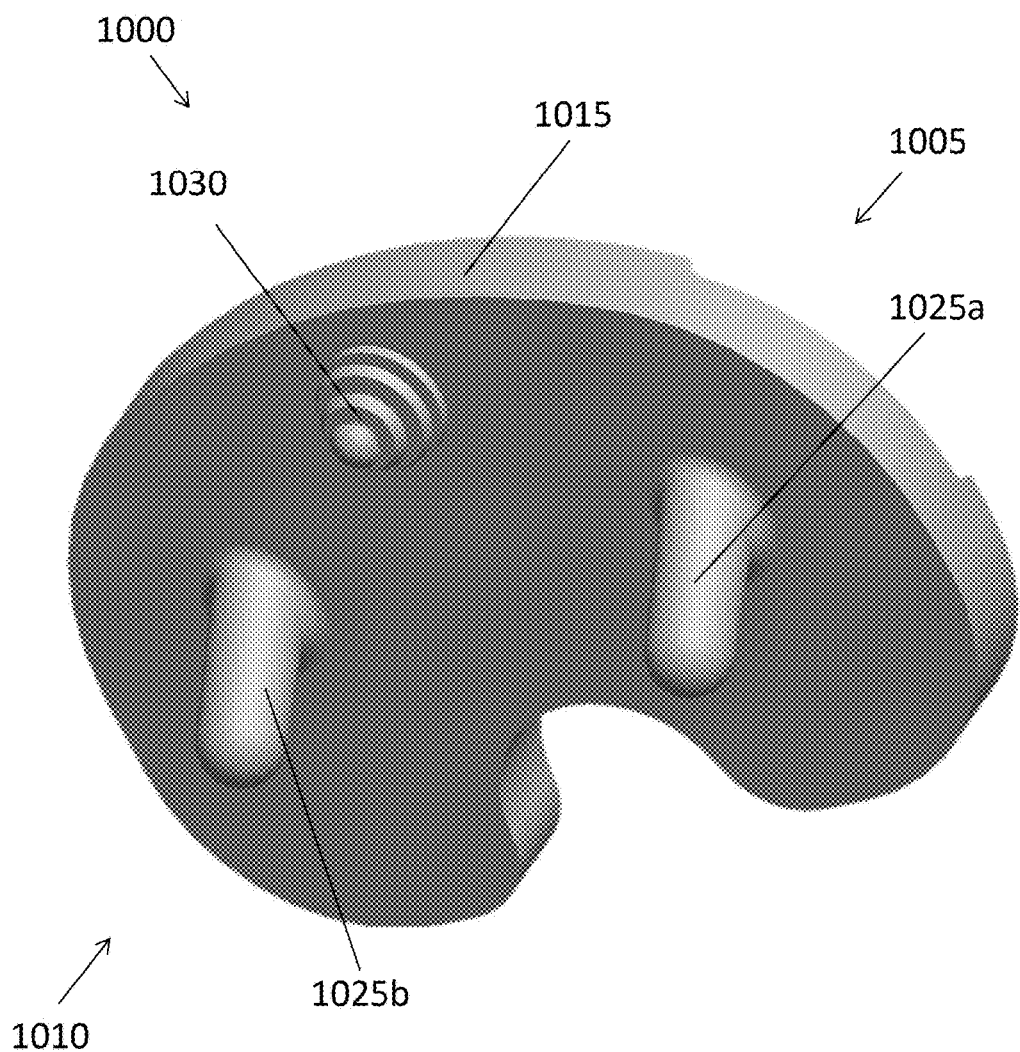
FIG. 10 is a bottom perspective view of a tibial baseplate according to another embodiment of the disclosure.
Figure 11:
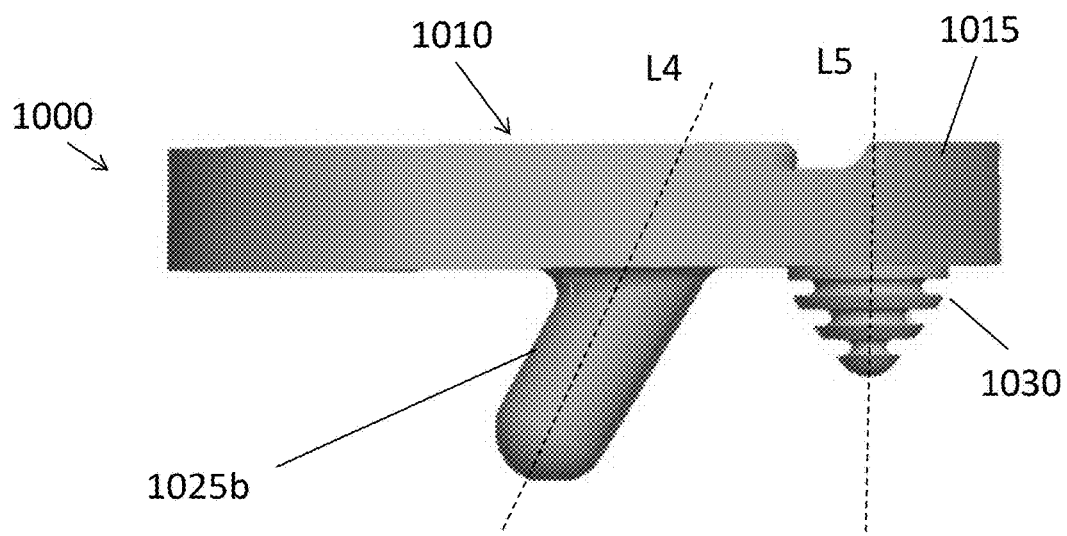
FIG. 11 is a side view of the tibial baseplate of FIG. 10.

Referring to FIGS. 10-11, there are shown bottom perspective and side views respectively, of a tibial baseplate or tray 1000 according to another embodiment of the disclosure. Baseplate 1000 includes a lateral condylar portion 1005 and a medial condylar portion 1010. Portions 1005, 1010 are designed to each receive a bearing insert, or otherwise receive a single bearing insert extending along both portions 1005, 1020 (not shown), such a UHMWPE bearing component. Lateral and medial condylar portions 1005, 1010 are connected by a bridge section 1015. However, in the embodiment shown for baseplate 1000, there is a less pronounced "U"-shape opening that may not accommodate the tibial eminence or the ACL/PCL. However, it should be understood that baseplate 1000 may be designed to retain both cruciate ligaments, similar to baseplate 100. Similarly, baseplate 100 may be designed instead not to retain the cruciate ligaments more similar to the shape of the embodiment of baseplate 1000 shown in FIG. 10.

Figure 12:
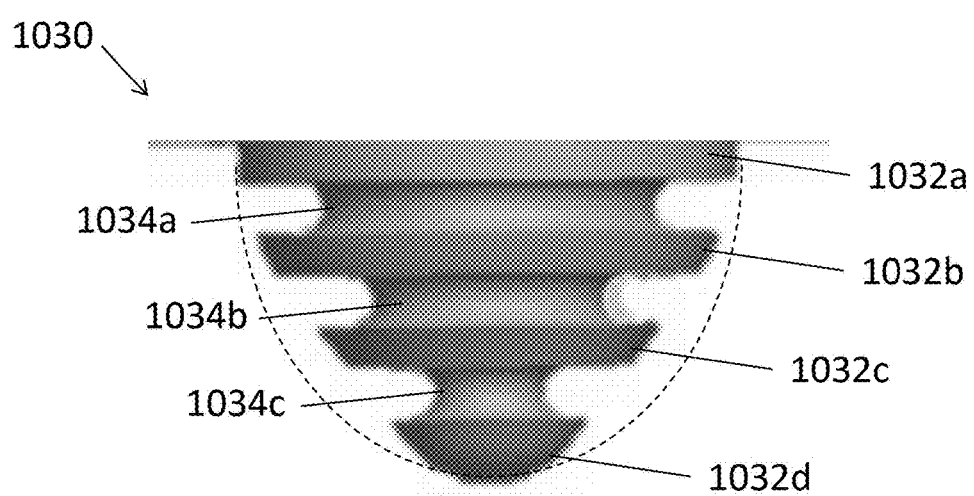
FIG. 12 is an enlarged isolated view of a fixation member of the tibial baseplate of FIG. 10.

Referring to FIGS. 10-12, the bottom surface of baseplate 1000 may include a first pair of fixation members 1025a,b and an anterior fixation members 1030. Fixation members 1025a may generally take the form of a peg extending inferiorly and posteriorly at an angle along a longitudinal axis L4, for example between approximately 20 degrees and approximately 60 degrees, from the bone-contact surface of the lateral condylar portion 1005 of the baseplate 1000. Peg 1025a may include a substantially cylindrical shaft portion that terminates in a blunted tip that has a substantially round or hemispherical shape. Medial condylar portion 1010 may include a fixation member 1025b in the form of a peg that is identical or substantially identical to peg 1025a, with the exception that peg 1025b extends from the bone contacting surface of the lateral condylar portion 1010 of baseplate 1000.

Fixation members 1025a and 1025b may be positioned at substantially equal locations in the anterior-posterior direction of baseplate 1000 with respect to one another. This position may be at or substantially at the center of the condylar portions 1005, 1010 in the anterior-posterior direction. As should be understood, the fixation members 1025a, 1025b may assist in securing the baseplate to a proximal tibia prepared to accept the baseplate 1000. In some embodiments, the baseplate 1000 may be forced, for example may impaction or another method, into the proximal tibia using force substantially aligned with the angle of the pegs 1025a, 1025b. In other embodiments, a pilot hole or a hole substantially matching the geometry of fixation members 1025a and 1025b may be formed in the proximal tibia to help guide the insertion of pegs 1025a, 1025b into the proximal tibia. Although pegs 1025a, 1025b are illustrated with blunted tips, other shapes may be acceptable including pointed tips, similar to those shown in connection with baseplate 100.

Anterior fixation member 1030 may be positioned on the bone contacting surface of baseplate 1000 at substantially the center in the medial-lateral direction and anterior to both fixation members 1025a, 1025b. An enlarged isolated side view of fixation member 1030 is shown in FIG. 12. Generally, fixation member 1030 includes radially projecting sections 1032a-d alternating with recessed sections 1034a-b. As best seen in FIG. 12, each radially projecting section 1032a-d may be substantially circular in cross section, with the distalmost section 1032d being blunted. It should be understood that although four such sections 1032a-d are illustrated, more or fewer sections may be sufficient. The outer circumference of each section 1032a-d may be generally flat (i.e. substantially parallel to the bone-contacting surface of baseplate 1000) or tapered inwardly toward an axis extending through the center of fixation member 1030. In other words, one or more sections 1032a-d may be tapered such that a portion of each section 1032a-d closer to the bone-contacting surface of the baseplate 1000 has a greater diameter and/or circumference than a portion of the respective section farther away from the bone-contacting surface of the baseplate 1000. With this tapered configuration, a line drawn to connect the profile of the edges of the sections 1032a-d would substantially have the shape of a parabola. Whether or not the edges of sections 1032a-d are tapered, it is preferably that the section 1032a closest to the bone-contacting surface has a relatively large diameter or width, and each additional section 1032b-d has a smaller diameter or width than the previous section. Between each pair of adjacent radially projecting sections 1032a-d is a recessed section 1034a-c. Each recessed section 1034a-c may be substantially cylindrical with a diameter smaller than that of each of the two adjacent projecting sections 1032a-d. Although the recessed sections 1034a-c may be substantially cylindrical, the outer surface of each section 1034a-c may have a curvature, for example a concave curvature as shown in FIG. 12.

Fixation member 1030 may be positioned substantially at the center of baseplate 1000 in the medial-lateral direction, and may be substantially equally spaced apart from fixation member 1025a and 1025b. Preferably, fixation member 1030 is positioned near an anterior end of the baseplate 1000 and anterior to both fixation members 1025a and 1025b.

In order to implant baseplate 1000, two angled holes may be created in the proximal tibia that correspond to the pair of fixation members 1025a-b, and a third hole may be created to accept fixation member 1030. However, any of the above holes may be omitted, particularly in connection with fixation member 1030. Similar to the method described in connection with baseplate 100, as the fixation members 1025a-b enter their respective holes in the proximal tibia, fixation member 1030 may drag along the proximal tibia and cause some amount of bone to dislodge from the tibia and enter the spaces around the recessed portions 1034a-c. Once fixation members 1025a,b and 1030 are positioned within their respective holes in the tibia, bone may begin to grow into the recesses 1034a-c of fixation member 1030, providing for increase fixation of the baseplate 1000 to the tibia. It should be noted that, although fixation members 1025a-b may each extend along a longitudinal axis L4 that is angled with respect to the bone-contacting surface of the baseplate 1000, fixation member 1030 may extend along a central longitudinal axis L5 that is substantially orthogonal to the bone-contacting surface of the baseplate 1000. Such a configuration may help resist the baseplate 1000 from becoming loose or otherwise uncoupling from the tibia.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial baseplate comprising:
    a superior surface and a bone-contacting surface opposite the superior surface;
    a medial condylar portion and a lateral condylar portion;
    a bridge portion connecting the medial and lateral condylar portions at an anterior end portion of the baseplate;
    first and second fixation members extending inferiorly from the bone-contacting surface of the medial condylar portions; and
    third and fourth fixation members extending inferiorly from the bone contacting surface of the lateral condylar portion,
    wherein each of the first and third fixation members extend posteriorly from the bone-contacting surface, is positioned anterior to the second and fourth fixation members respectively, includes at least one recessed surface extending continuously from the bone-contacting surface to a pointed tip of the respective fixation member, and includes a non-recessed anterior surface extending continuously from the bone-contacting surface to the tip of the respective fixation member at a first angle relative to the bone-contacting surface,
    wherein each of the second and fourth fixation members include a shaft extending posteriorly from the bone-contacting surface to a pointed tip of the respective fixation member at a second angle relative to the bone-contacting surface, the second angle being equal to or greater than the first angle.

2. The tibial baseplate of claim 1, wherein the at least one recessed surface of each of the first and third fixation members includes a lateral recess, a posterior recess, and a medial recess.

3. The tibial baseplate of claim 2, wherein each of the first and third fixation members includes a posterior-medial wall and a posterior-lateral wall that converge with the non-recessed anterior surface to form the tip, the lateral recess, the posterior recess, and the medial recess.

4. The tibial baseplate of claim 1, wherein the pointed tips of the first and third fixation members each extend along a longitudinal axis orthogonal to the bone contacting surface.

5. The tibial baseplate of claim 1, wherein the shafts of the second and fourth fixation members are each cylindrical.

6. The tibial baseplate of claim 1, wherein the second angle is between 20 degrees and 60 degrees.

7. The tibial baseplate of claim 1, wherein the pointed tips of the second and fourth fixation members have a conical shape.

8. The tibial baseplate of claim 1, wherein the second and fourth fixation members are positioned at equal locations in an anterior-to-posterior direction of the baseplate with respect to one another.

9. The tibial baseplate of claim 1, wherein the second fixation member is positioned at a center of the medial condylar portion in an anterior-to-posterior direction of the baseplate, and the fourth fixation member is positioned at a center of the lateral condylar portion in the anterior-to-posterior direction of the baseplate.

10. The tibial baseplate of claim 9, wherein the second and fourth fixation members are positioned at offset locations in the anterior-to-posterior direction of the baseplate with respect to one another.

11. The tibial baseplate of claim 1, wherein the medial condylar portion and the lateral condylar portion define an opening therebetween for accommodating a tibial eminence of a patient.

12. The tibial baseplate of claim 11, wherein the opening is positioned between the second and fourth fixation members.

13. The tibial baseplate of claim 1, wherein the first fixation member is positioned closer to a mid-line of the baseplate than is the second fixation member, the mid-line extending in an anterior-to-posterior direction of the baseplate and separating the medial and lateral condylar portions.

14. The tibial baseplate of claim 13, wherein the third fixation member is positioned closer to the mid-line than is the fourth fixation member.

15. The tibial baseplate of claim 1, wherein the pointed tips of the first and third fixation members are each formed along an axis that is orthogonal to the bone-contacting surface.

16. The tibial baseplate of claim 1, wherein the first and third fixation members are integral with the baseplate.

17. The tibial baseplate of claim 1, wherein the second and fourth fixation members are integral with the baseplate.

* * * * *